United States Patent [19]

Strawn

[11] Plant 4,638

[45] Feb. 3, 1981

[54] MINIATURE ROSE PLANT

[76] Inventor: Leslie E. Strawn, 10422 Morningside Ave., Garden Grove, Calif. 92643

[21] Appl. No.: 94,816

[22] Filed: Nov. 15, 1979

[51] Int. Cl.[3] ..... A01H 5/00

[52] U.S. Cl. ..... Plt./9

[58] Field of Search ..... Plt./9

*Primary Examiner*—Robert E. Bagwill

[57] ABSTRACT

The subject of the present disclosure is a new and distinct variety of miniature rose plant characterized by deep coral pink buds and flowers of distinctive form and further identified by the neat, dwarf, compact plant.

1 Drawing Figure

1

The present invention relates to a new and distinct variety of hardy, dwarf, bush type rose plant of the miniature class; the variety being primarily characterized—as to novelty—by the deep coral pink buds and flowers which in general color effect are similar to Hula Girl (miniature—U.S. Plant Pat. No. 4,091).

The variety is further characterized by:

The unique buds and flowers.

An abundance of bloom, with flowers borne singly or with one, two or three side buds.

Light sweet fragrance.

A plant which is vigorous, of an upright growth habit with small semi-glossy foliage with pointed leaflets; the buds and flowers being similar in form and size to Sheri Anne (miniature—U.S. Plant Pat. No. 3,826) the pollen parent.

The plant, which grows and blooms satisfactorily both in greenhouse and outdoors; is good for growing in pots; and provides excellent garden decoration as well as cut flowers.

A plant which has a normal height of 12 to 14 inches and can easily be maintained at a lesser height by occasional trimming.

The present variety of miniature rose was originated by me in my home greenhouse, located at Garden Grove, Orange County, Calif., under conditions of careful control and observation, as a cross between Liverpool Echo (floribunda rose—non patented) as the seed parent and Sheri Anne (miniature—U.S. Plant Pat. No. 3,826) as the pollen parent.

Subsequent to origination of the variety I successfully asexually reproduced it in my garden, located as foresaid (also propagated by Pixie Treasures Rose Nursery, 4121 Prospect Ave., Yorba Linda, Orange County, Calif. by cuttings as well as by budding; the reproductions having run true in all respects.

The color photograph illustrates the variety, including foliage, buds and flowers.

Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy; dwarf; upright; rounded; seedling; greenhouse; outdoors; cut flowers; garden decoration; potted plant.

Class: Miniature.

*Variety name.*—Crissy.

2

Flowers borne: Singly or with side buds on upright stems.

Quantity of bloom: Abundant, both outdoors and in greenhouse.

Bud:

*Peduncle.*—Short; slender but sturdy; erect; light green, tinted bronze (outdoors); Hairs—covered.

*Before calyx breaks.*—Size—small. Form—pointed; medium long; with foliaceous parts extending beyond tip of bud equal to one half of its length. Color—medium green.

*As calyx breaks.*—Near vermilion 18/2 with white area toward base showing and inside petal color, near vermilion 18/1 barely visable along edges. Opening—opens well in all weather.

Bloom:

*Size when fully open.*—Small, averaging about 4 cm (1½").

*Petalage.*—Double—averaging about 20 to 25 petals, arranged regularly, plus one or two petaloids.

*Form.*—Full, at first, becoming rounded with medium high center, petals reflex slightly except for pointed tips, which point out. Stamens show when fully open.

Petals: Fairly thick; satiny on inside and outside surfaces.

*Shape.*—Outside petals—equally broad as its depth with a definite point at apex, and a rounded base; intermediate petals—slightly less broad than its depth, with a pointed apex and a rounded base; inside petals—width equal to two thirds of its depth, with a wedge shaped base, apex less pointed. All petals having a faint inverted pleat through the centers.

Color: One half to three quarters open flowers from a plant grown outdoors at Pixie Treasures Rose Nursery, Yorba Linda, Calif., October 1979.

*Outside petal.*—Outside surface—near Vermilion 18/2 on the outer three quarter area, becoming slightly lighter towards base; base area near white. Inside surface—near Vermilion 18/1 blending close to Vermilion 18/2 towards center; base area near white or greenish white.

*Intermediate petal.*—Outside surface—same as outside petal; Inside surface—same as outside petal.

*Inside petal.*—Outside surface—same as outside petal but in addition to, may have a faint near white streak through center; Inside surface—same as outside petal.

General color effect:

*Newly opened flowers.*—Symmetrical arrangement of clear, vibrant, deep coral pink petals.

*Three days open.*—Color similar to newly open flowers, may be slightly lighter.

Behavior: Opens well in all weather. Spent petals drop off (separates at top of calyx tube). Hips form readily. Flower Longevity (October 1979)—plant in ground 5-6 days or longer, plant in pot—4-5 days or longer; cut flowers at living room temperature—4-5 days or longer.

Reproductive organs:

*Stamens.*—40 to 50, uneven lengths.

*Filaments.*—Pale whitish green.

*Anthers.*—Golden yellow, introrse.

*Pollen.*—Moderate amount.

*Pistils.*—Projects above disc.

*Styles.*—Several, bunched, may be tinted pink.

*Ovaries.*—All enclosed in calyx.

*Hips.*—Form readily.

*Sepals.*—Permanent, spear shaped, reflexed.

*Seed.*—Set seed readily, moderate number.

Foliage:

*Leaves.*—Compound of five or seven leaflets—usually five; small—varying from 4 cm to 8 cm length; leathery semi-glossy.

*Leaflets.*—Shape—ovate, acute apex, base rounded; almost no petiolule; margin serrate.

*Rachis.*—Very slender; upper side grooved; few hairs; underside may have few needle shaped thorns.

*Stipules.*—Hairs on edge; auricles very pointed and flaring outward 60 to 90 degrees.

*Color.*—Medium green; rachis and serrated edges sometimes tinted bronze.

Growth:

*Habit.*—Dwarf, bushy; erect; much branched; rounded.

*Growth.*—Vigorous; internodes short.

*Canes.*—Medium; slender; sturdy.

*Main stems.*—Color—medium green.

*Thorns.*—Very few; needle shape; projects at right angle to stems; 3 to 5 mm; color—pink to tan.

*Branches.*—Color—medium to light green; thorns—very few; medium base; prickles—none; hairs—none; young shoots—color—reddish green, thorns—reddish.

The miniature rose plant and its flowers as herein described may vary in slight detail due to climatic, soil and cultural conditions under which the variety may be grown.

The following is claimed:

1. A new and distinct variety of miniature rose plant of hardy, dwarf, bushy, erect, much branched habit, substantially as illustrated and described, characterized by buds and flowers which are of a clear, vibrant, deep coral pink, the buds and flowers, in general color effect, similar to Hula Girl (miniature—U.S. Plant Pat. No. 4,091) and Sheri Anne (miniature—U.S. Plant Pat. No. 3,826) in vigor, form and size, the buds and flowers having a distinct and unique appearance as compared to other miniature roses of its color class, said flowers being very double, of symmetrical form; and further characterized by a plant which is vigorous, with compact growth habit, and easy to propagate from soft wood cuttings, or by budding and bearing an abundance of flowers.

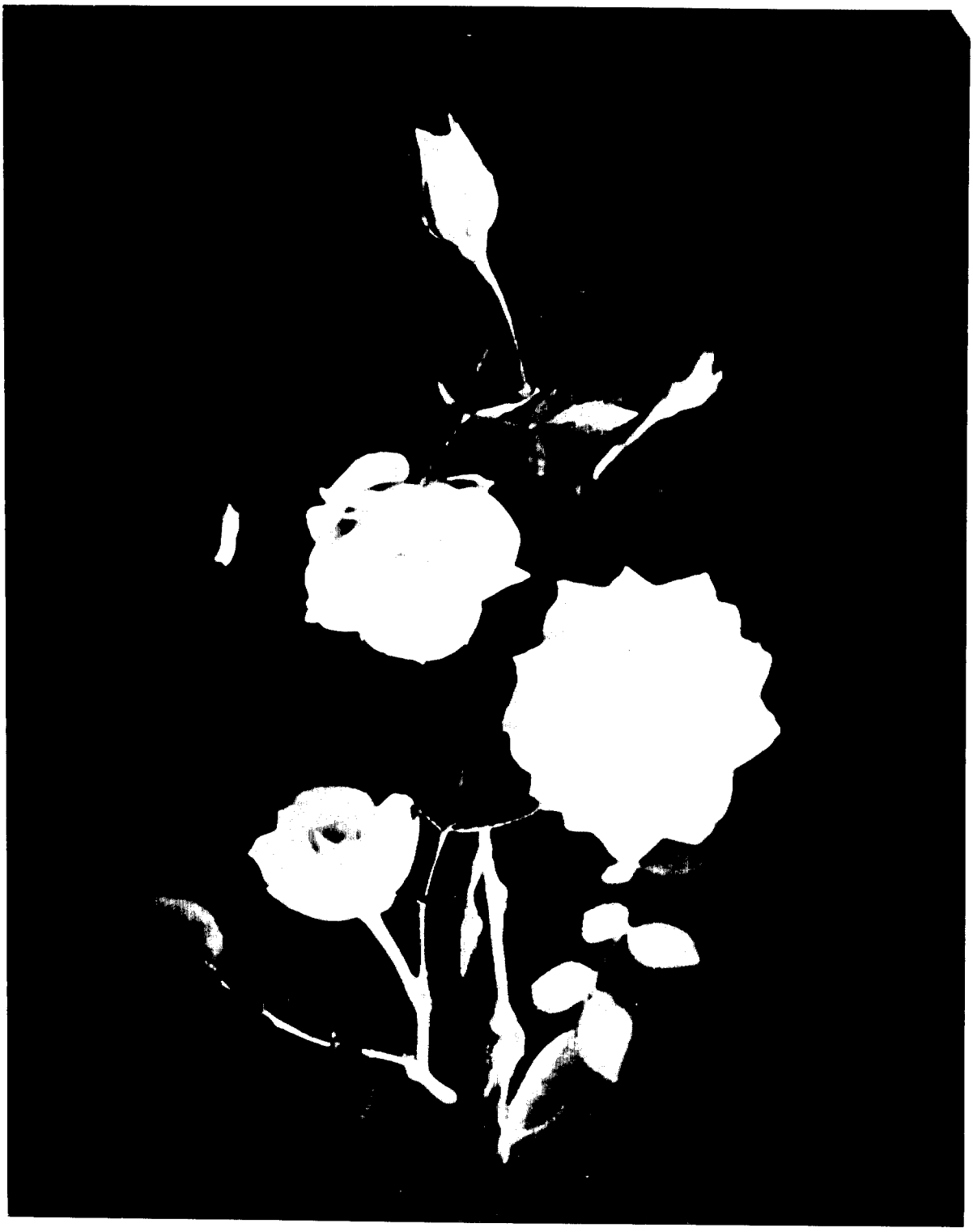

* * * * *